United States Patent
Yang et al.

(10) Patent No.: US 10,369,031 B2
(45) Date of Patent: Aug. 6, 2019

(54) DELIVERY AND RELEASE DEVICE FOR STENT-GRAFT

(71) Applicant: BEIJING PERCUTEK THERAPEUTICS CO., LTD., Beijing (CN)

(72) Inventors: Fan Yang, Beijing (CN); Jiahua Xiao, Beijing (CN); Jing Xu, Beijing (CN)

(73) Assignee: BEIJING PERCUTEK THERAPEUTICS CO., LTD, Beijing (CN)

( * ) Notice: Subject to any disclaimer, the term of this patent is extended or adjusted under 35 U.S.C. 154(b) by 428 days.

(21) Appl. No.: 14/360,498

(22) PCT Filed: Nov. 23, 2012

(86) PCT No.: PCT/CN2012/085208
§ 371 (c)(1),
(2) Date: May 23, 2014

(87) PCT Pub. No.: WO2013/075664
PCT Pub. Date: May 30, 2013

(65) Prior Publication Data
US 2014/0343659 A1  Nov. 20, 2014

(30) Foreign Application Priority Data

Nov. 25, 2011  (CN) .......................... 2011 1 0380897

(51) Int. Cl.
*A61F 2/966* (2013.01)
*A61F 2/07* (2013.01)

(52) U.S. Cl.
CPC ................ *A61F 2/966* (2013.01); *A61F 2/07* (2013.01); *A61F 2002/9665* (2013.01)

(58) Field of Classification Search
CPC .... A61F 2/07; A61F 2/95; A61F 2/954; A61F 2/958; A61F 2/962; A61F 2/966;
(Continued)

(56) References Cited

U.S. PATENT DOCUMENTS 5,387,235 A    2/1995  Chuter
6,786,918 B1 *  9/2004  Krivoruchko ............. A61F 2/95
                                                606/108

(Continued)

FOREIGN PATENT DOCUMENTS

CN         2548564 Y      5/2003
CN       101045022 A     10/2007
(Continued)

*Primary Examiner* — Elizabeth Houston
*Assistant Examiner* — Kankindi Rwego
(74) *Attorney, Agent, or Firm* — Reches Patents

(57) ABSTRACT

A delivery and release device for stent-graft includes a guiding head and a central tube connected thereto, an outer tube sleeving on the outside of the central tube, a positioning tube sheathed between the central tube and the outer tube, a front fixator, a back fixator and a positioner successively sheathed between the positioning tube and the outer tube. The stent-graft is placed between the back fixator and the positioner. A metal bar is connected to the guiding head along its axial direction with a ring suture being connected to the front fixator. The ring suture sleeves onto the metal bar after passing through the stent-graft. During the release process, the metal bar moves forward in the axial direction to detach from the ring suture, thereby the stent-graft is released.

9 Claims, 11 Drawing Sheets

(58) Field of Classification Search
CPC ............... A61F 2/97; A61F 2002/072; A61F 2002/075; A61F 2002/077; A61F 2002/9505; A61F 2002/9511; A61F 2002/9517; A61F 2002/9522; A61F 2002/9528; A61F 2002/9534; A61F 2002/9583; A61F 2002/9586; A61F 2002/9665; A61F 2002/011; A61F 2/2427; A61F 2/2439
USPC ........................................ 623/1.11, 1.12, 2.11
See application file for complete search history.

(56) References Cited

U.S. PATENT DOCUMENTS

| | | | | |
|---|---|---|---|---|
| 7,147,657 B2* | 12/2006 | Chiang | ............... | A61F 2/07 623/1.11 |
| 2003/0233140 A1* | 12/2003 | Hartley | ............... | A61F 2/95 623/1.11 |
| 2005/0288768 A1* | 12/2005 | Sowinski | ............... | A61F 2/07 623/1.13 |
| 2007/0260301 A1* | 11/2007 | Chuter | ............... | A61F 2/95 623/1.11 |
| 2008/0114435 A1* | 5/2008 | Bowe | ............... | A61F 2/95 623/1.11 |
| 2009/0099637 A1 | 4/2009 | Barthold et al. | | |
| 2009/0099640 A1 | 4/2009 | Weng | | |
| 2010/0082089 A1* | 4/2010 | Quadri | ............... | A61F 2/2418 623/1.11 |
| 2010/0125322 A1* | 5/2010 | Fitzgerald | ............... | A61F 2/95 623/1.11 |

FOREIGN PATENT DOCUMENTS

| | | |
|---|---|---|
| CN | 102488576 A | 6/2012 |
| CN | 202397529 U | 8/2012 |
| WO | WO 2007/011510 A2 | 1/2007 |

* cited by examiner 1    guiding head 2    metal bar (bar-shaped body)

28   ring suture (string-shaped body)

3    front fixator 4    back fixator

SG   bare stent of the stent-graft 6    positioning tube 7    central tube 8    outer tube FIG. 12A
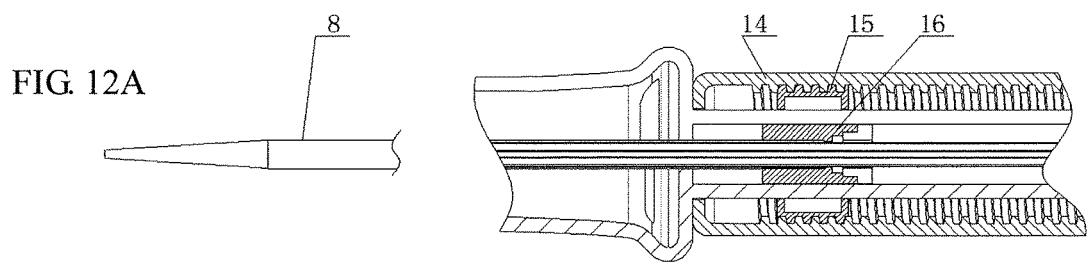
FIG. 12B
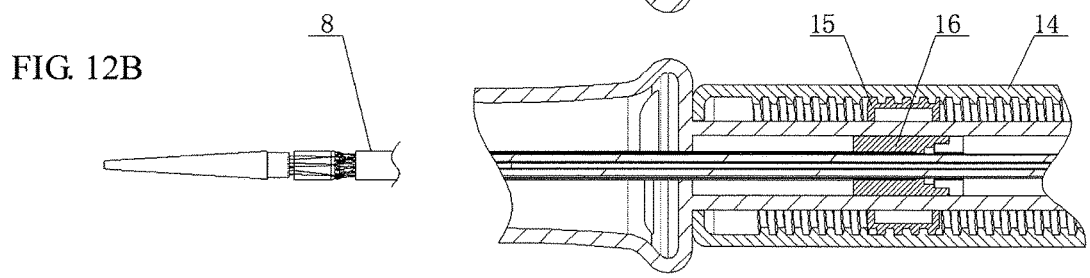
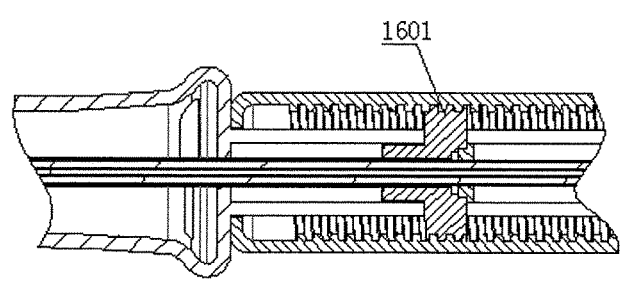
FIG. 13

DELIVERY AND RELEASE DEVICE FOR STENT-GRAFT

TECHNICAL FIELD

The present invention belongs to the field of medical apparatus and instruments, and especially relates to a delivery and release device for stent-graft for treatment of aortic aneurysm and aortic dissection.

BACKGROUND OF THE INVENTION

Aortic aneurysm and aortic dissection are relatively dangerous vascular diseases that are commonly found clinically, and without duly treatment they might endanger the patient's life because of aortic rupture; traditional methods of surgical operation have low success rate of cure, and high risks.

Interventional therapy of aortic aneurysm and aortic dissection is a new piece of technology applied clinically in recent years. Its principle is that a length of stent-graft with suitable dimension is preloaded into a delivery and release device, then guided into the human body, and under surveillance of X-ray monitoring equipment, the stent-graft is released at the diseased region of the aorta and conformed tightly onto the aortic vessel wall, so as to block the blood acquiring channel of the diseased region and to gradually form thrombus at the diseased region of the aorta, thereby the risk of massive hemorrhage caused by aortic rupture is eliminated, and the therapeutic purpose is achieved.

In prior art, the patent CN2548564Y disclosed a delivery and release device for abdominal aorta stent-graft, which comprises a mandrel and a sleeve, wherein, the mandrel comprises a guiding head at the front and an inner tube connected on the rear side of the guiding head for the stent-graft to be sheathed thereon, the mandrel also comprises a slidable pushrod and a central tube, and a through hole extending axially through the mandrel is formed in the center of the mandrel; the sleeve is a hollow structure and integrally sleeves on the mandrel at the rear side of the guiding head, the front part of the sleeve is an outer sheath tube, the rear part of the sleeve is a connecting base with a liquid injection port, the outer sheath tube is slidably coordinating with the pushrod in the axial direction, and a space for placing the stent-graft is formed between the inner tube and the outer sheath tube; a rotatable shaft is provided inside the sleeve, the rotatable shaft is supported on the guiding head by a rotation fulcrum, a controlling suture is provided on the rotatable shaft, one end of the suture is wound around the rotatable shaft, the other end of the suture passes through the stent-graft and is tightened, during usage, by rotating the rotatable shaft to release the controlling suture, the front end of the stent-graft is released.

In the above-mentioned technical solution, because the length-diameter ratio of the rotatable shaft for releasing the controlling suture to release the stent-graft is relatively large, when rotating the handle at the tail end of the rotatable shaft to control the shaft, the torque is not able to be effectively transmitted, which leads to difficulty in the operation of releasing the stent-graft; also, when rotating the rotatable shaft to release the stent-graft, it is possible for the already positioned stent-graft delivery and release device to shift its position, thus cause the position of the stent-graft to shift, which leads to inaccuracy of the release position of the stent-graft; furthermore, when releasing the stent-graft, it is required to rotate the rotatable shaft in order to release the controlling suture to allow the suture to stretch, however, there is a lot of uncertainty in the winding manner of the controlling suture, and possible problems of knotting or crossing of the controlling suture might cause the controlling suture to be not able to stretch, which leads to failure in releasing the stent-graft.

As an alternative solution to the problem in the above-mentioned technology of difficulty in releasing the stent-graft, U.S. Patent US2009099637A1 discloses a delivery and release device for stent-graft, a guiding head of this device is connected to and internally communicated with a central tube at the rear side, an outer tube sleeves on the central tube at the rear side of the guiding head, a larger end of the guiding head is provided with metal bars fixed thereon in the axial direction, a locking member is arranged close to the guiding head and sheathed between the outer tube and the central tube, the locking member is provided with a through hole to form a detachable connection with the metal bars, a positioning tube is sheathed between the locking member and the central tube and passes through the locking member; when loading the device, the stent-graft is tightened and sheathed between the positioning tube and the central tube, and the metal bars are guided through projecting loops at the proximal end (the end proximal to the heart) of the stent-graft and then inserted into the through hole so as to fasten the stent-graft, and when using the device, the outer tube is first pulled backwards to release the rear part of the stent-graft, and then the central tube is pushed forwards to drive the metal bars on the guiding head to move forwards and detach from the locking member, thereby completely releasing the stent-graft. In this technology, the way of releasing the stent-graft by using a central tube to drive metal bars on a guiding head to detach from a through hole in a locking member so as to separate the metal bars from the locking member and the projecting loops at the proximal end of the stent-graft is simple to operate and easy to implement, and solves the problems in the above-mentioned technology such as difficulty in the operation of releasing the stent-graft, inaccuracy of the release position and low success rate of release; however, in this technology, rigid metal bars are utilized to pass through the projecting loops at the proximal end of the stent-graft and then be inserted into the locking member so as to be fastened, as the volume of the stent-graft is very small and the projecting loops at its proximal end are also very small, the metal bars need to be machined into a size small enough to pass through the projecting loops of the stent-graft, which puts high requirements on precision of machining and thus increases the cost, and also as the material used for producing the stent-graft is low in hardness, the rigid metal bars passing through the projecting loops of the stent-graft might easily cause permanent deformation of the proximal end of the stent-graft, and when released into a human body for utilization, the deformed stent-graft might not be conformed to the blood vessel firmly at the deformed part, as a result, blood leakage occurs, and more catastrophically, the stent-graft does not function as expected and the operation becomes a failure.

SUMMARY OF THE INVENTION

One objective of the present invention is to solve the technical problem that, in prior art, the delivery and release device for stent-graft releases the stent-graft by rotate a rotatable shaft, which is difficult to operate, the stent-graft tend to shift its position driven by the rotatable shaft, which leads to inaccuracy of positioning, and there is uncertainty in the winding manner of the controlling suture, which causes knotting, crossing and incapacity to stretch of the controlling suture, and leads to failure in releasing the stent-graft; thus, the present invention provides a delivery and release device for stent-graft wherein the operation is simple, the positioning is accurate and the success rate of releasing is high when releasing the stent-graft.

Another objective of the present invention is to solve the technical problem that, in prior art, when releasing the stent-graft by using a central tube to drive rigid metal bars on a guiding head to detach from the through hole in a locking member and projecting loops at the proximal end of the stent-graft, as the metal bars have to be small enough to pass through the projecting loops of the stent-graft, the requirements on precision of machining the metal bars are high and thus the cost is high, and also as the material of the stent-graft is low in hardness, the rigid metal bars passing through the projecting loops of the stent-graft might easily cause permanent deformation of the proximal end of the stent-graft, as a result, the stent-graft might not be conformed to the blood vessel firmly, which leads to blood leakage or even failure of releasing the stent-graft; thus, the present invention provides a delivery and release device for stent-graft wherein the cost is low, and no permanent deformation of the stent-graft occurs.

To solve the aforementioned technical problems, the present invention provides a delivery and release device for stent-graft, comprising:

a guiding head, in the shape of a cone, and provided with a hollow passage formed axially therein;

a central tube, one end of which is fixedly connected to a larger end of the guiding head and communicated with the hollow passage of the guiding head;

an outer tube, sleeving on the exterior of the central tube, and operable to slide along the exterior of the central tube;

a fixator, sheathed between the central tube and the outer tube, with an outer periphery of the central tube close to the larger end of the guiding head sheathed by the fixator, and with an outer periphery of the fixator coordinating with an inner periphery of the outer tube in a sliding manner;

a positioning mechanism, adapted for positioning the stent-graft;

an outer tube displacement regulating mechanism, sleeving on an outer periphery of the outer tube at an operation side, and adapted for controlling the axial movement of the outer tube;

a central tube displacement regulating mechanism, sleeving on the central tube at an operation side, and adapted for controlling the axial movement of the central tube;

wherein, a tightening and releasing means for the stent-graft is provided at the larger end of the guiding head, the tightening and releasing means comprises a flexible tightening member, the flexible tightening member is connected to the larger end of the guiding head for tightening the stent-graft, and the central tube is operable to control the guiding head to move in the axial direction of the central tube, so as to detach the flexible tightening member from the stent-graft, thereby releasing the stent-graft.

The positioning mechanism comprises a positioning tube and a positioner, the positioning tube is sheathed between the fixator and the central tube and extends through the fixator, the positioner is sheathed between the positioning tube and the outer tube, with an outer periphery of the positioning tube at a rear side of the stent-graft sheathed by the positioner, and with an outer periphery of the positioner coordinating with an inner periphery of the outer tube in a sliding manner.

The delivery and release device for stent-graft further comprises a supporting mechanism, which comprises a supporting tube sheathed between the positioning tube and the outer tube, and a supporting tube holder, with one end of the supporting tube fixedly connected to the rear end of the positioner and the other end connected to the outer tube displacement regulating mechanism by the supporting tube holder.

The positioner is a hollow tubular structure, with texture formed on its outer periphery, the central tube and the positioning tube extend through the positioner.

The fixator comprises a front fixator and a rear fixator, the front fixator and the rear fixator are sheathed between the positioning tube and the outer tube respectively at the front side and at the rear side, the rear fixator is provided with a conical anti-rotation member at its rear end for preventing the stent-graft from rotating, the conical anti-rotation member is sheathed between the positioning tube and the outer tube, and a plurality of anti-rotation recesses are formed axially on an outer periphery of the conical anti-rotation member.

The outer tube displacement regulating mechanism comprises a front stopper, an outer shell, a rear stopper, and a regulating means provided on the exterior of the outer shell for controlling the displacement of the outer tube, one end of the outer shell is fixedly connected to the front stopper coaxially, and the other end of the outer shell is fixedly connected to the rear stopper coaxially, the supporting tube holder is disposed inside the outer shell and in fixed connection with the outer shell; the regulating means is disposed between the front stopper and the rear stopper, the rear ends of the outer tube and the positioning tube are respectively connected to the regulating means, and the regulating means is operable to be adjusted to move along the outer shell, so as to drive the outer tube to move axially.

The regulating means comprises an outer motion-transmission sleeve and an inner motion-transmission sleeve sleeving on the outer shell, and an outer tube holder fixedly connected to a rear end of the outer tube, the inner motion-transmission sleeve is disposed inside the outer motion-transmission sleeve and the two motion-transmission sleeves are engaged in a threaded connection, the outer tube holder is sheathed inside the outer shell and provided with connectors fixedly connected on both sides thereof, the outer shell is provided with elongated apertures formed thereon and extending in the axial direction, and the connectors extend through the elongated apertures to be connected to the inner motion-transmission sleeve.

The central tube displacement regulating mechanism is provided at the rear side of the outer tube displacement regulating mechanism and comprises a central tube positioning sleeve and a regulating rotary handle, the rear end of the central tube is fixed inside the central tube positioning sleeve, the regulating rotary handle is arranged to sleeve on the exterior of the central tube positioning sleeve and is in a threaded connection therewith; one end of the central tube positioning sleeve is fixedly connected to a rear end of the outer shell and provided with elongated apertures formed thereon and extending in the axial direction of the central tube, connectors are formed on an outer periphery of the central tube at its rear end, the connectors extend through the elongated apertures on the central tube positioning sleeve to be sheathed inside the regulating rotary handle, and the regulating rotary handle is operable to be rotated, so as to drive the central tube to move axially.

The tightening and releasing means further comprises a releasing member connected to the larger end of the guiding head, one end of the flexible tightening member is connected to the front fixator, while the other end of the flexible tightening member passes through a proximal end of the stent-graft and is detachably connected to the releasing member; the releasing member is detachable from the flexible tightening member, driven by the axial movement of the guiding head, so as to release the stent-graft.

The tightening and releasing means further comprises a releasing member connected to the front fixator, one end of the flexible tightening member is connected to the larger end of the guiding head, while the other end of the flexible tightening member passes through a proximal end of the stent-graft and is detachably connected to the releasing member by tying, sleeving, buckling or magnetic attraction; the flexible tightening member is detachable from the releasing member, driven by the axial movement of the guiding head, so as to release the stent-graft.

The flexible tightening member is detachably connected to the releasing member by tying, sleeving, buckling or magnetic attraction.

The releasing member is a bar-shaped body extending in the axial direction of the central tube, and one end of the bar-shaped body is connected to the end face of the larger end of the guiding head, while the other end of the bar-shaped body is detachably connected to the flexible tightening member; the flexible tightening member is a string-shaped body, and one end of the string-shaped body is connected to the front fixator, while the other end of the string-shaped body passes through a proximal end of the stent-graft and is detachably connected to the bar-shaped body; the bar-shaped body is detachable from the string-shaped body, driven by the axial movement of the guiding head, so as to release the stent-graft.

A through hole is axially formed through the front fixator, and adapted for detachably connecting the front fixator to the bar-shaped body.

The bar-shaped body is a metal bar connected to the end face of the larger end of the guiding head and positioned circumferentially on the end face, and the string-shaped body is a ring suture, the ring suture is detachably connected to the metal bar by sleeving.

A reinforcement tube is arranged to sleeve on an outer periphery of the supporting tube, one end of the reinforcement tube extends through the outer tube holder and is placed inside the front stopper, while the other end of the reinforcement tube is fixedly connected to a reinforcement tube holder, and the reinforcement tube holder is fixed inside the outer shell and close to the supporting tube holder.

The central tube positioning sleeve is integrally formed with the outer shell, each end of the central tube positioning sleeve is provided with a hoop connected and sleeving thereon, with one hoop arranged to sleeve on the rear end of the outer shell and with the other hoop arranged to sleeve on the tail end of the central tube positioning sleeve.

Compared to prior art, the present invention has the following beneficial effects:

(1) In the delivery and release device for stent-graft of the present invention, the guiding head has a tightening and releasing means for the stent-graft provided at the larger end thereof, which comprises a flexible tightening member, the flexible tightening member is connected to the larger end of the guiding head for tightening the stent-graft, and the central tube is operable to control the guiding head to move in the axial direction of the central tube, so as to detach the flexible tightening member from the stent-graft, thereby releasing the stent-graft. When loading the stent-graft, the flexible tightening member passes through the projecting loop at the proximal end of the stent-graft, tightens the stent-graft and is connected to the larger end of the guiding head for tightening the stent-graft; when the delivery and release device releases the stent-graft after being positioned inside a human body, the central tube is controlled to drive the guiding head to move forwards in the axial direction, so as to detach the flexible tightening member from the stent-graft and allow the stent-graft to unfold and be released under its own elastic force. In the aforementioned process, the operation of using a central tube to drive a guiding head to move in the axial direction so as to detach the flexible tightening member from the stent-graft and release the stent-graft is simple to operate, with a high success rate of releasing the stent-graft, the position of the already positioned stent-graft is not changed during the releasing process, and the stent-graft is tightened and released by a flexible tightening member, so that no permanent deformation of the stent-graft occurs, and the requirements on machining precision of the flexible tightening member is not high, which does not need high cost.

(2) In the delivery and release device for stent-graft of the present invention, a positioning tube is sheathed between the fixator and the central tube and extends through the fixator, and a positioner is arranged at the rear side of the stent-graft and sheathed between the positioning tube and the outer tube, with an outer periphery of the positioner coordinating with an inner periphery of the outer tube in a sliding manner. When loading the stent-graft, the outer tube is covered on the exterior of the already tightened stent-graft, and the front and rear ends of the stent-graft are respectively constrained by the fixator and the positioner, so as to prevent axial movement of the stent-graft inside the delivery and release device and thus ensure that the delivery and release device can accurately position the stent-graft after being introduced into a human body; the positioning tube is sheathed on the exterior of the central tube, the fixator, the stent-graft and the positioner are sheathed between the positioning tube and the outer tube, when controlling the central tube to drive the guiding head to move forwards in the axial direction, because the positioning tube does not move, the fixator, the stent-graft and the positioner do not move forwards along with the central tube, but stay in original position, therefore, as the guiding head moves forwards, the flexible tightening member connected thereto is detached from the stent-graft, and the stent-graft is released and unfolds, thus the arrangement of the positioning tube ensures successful release of the stent-graft.

(3) In the delivery and release device for stent-graft of the present invention, a supporting tube is sheathed between the positioning tube and the outer tube, with one end of the supporting tube fixedly connected to the rear end of the positioner and the other end connected to the outer tube displacement regulating mechanism by a supporting tube holder. In the delivery and release device, the supporting tube is fixed onto the controlling mechanism of the outer tube by the supporting tube holder so that the position of the supporting tube is confined, meanwhile the supporting tube is fixedly connected to the rear end of the positioner so that the position of the rear end of the positioner is confined, thus the supporting tube indirectly confines the position of the rear end of the stent-graft, so as to prevent the stent-graft from moving backwards in the axial direction.

(4) In the delivery and release device for stent-graft of the present invention, the positioner is a hollow tubular structure, with texture formed on its outer periphery, the central tube and the positioning tube extend through the positioner. The hollow tubular structure of the positioner makes it easy to sheathe the positioner between the positioning tube and the outer tube; when the stent-graft has not been released yet, the outer tube covers on the exterior of the stent-graft, and the positioner is arranged at the rear side of the stent-graft, at this state, if the stent-graft is not completely tightened, it is possible that the stent-graft expands to render its radial dimension larger than the radial dimension of the positioner, and then it is possible for the stent-graft to move axially, therefore, under this circumstance, the texture on the outer surface of the positioner is able to further confine the stent-graft to prevent it from moving backwards in the axial direction.

(5) In the delivery and release device for stent-graft of the present invention, the fixator comprises a front fixator and a rear fixator, the front fixator and the rear fixator are sheathed between the positioning tube and the outer tube respectively at the front side and at the rear side, the rear fixator is provided with a conical anti-rotation member at its rear end for preventing the stent-graft from rotating, the conical anti-rotation member is sheathed between the positioning tube and the outer tube, and a plurality of anti-rotation recesses are formed axially on an outer periphery of the conical anti-rotation member. As the present device tightens the stent-graft by guiding a flexible tightening member through the projecting loop on the stent-graft, the conical anti-rotation member is able to prevent the already tightened stent-graft from rotating, so as to prevent the problem of intertwining, crossing or knotting of the flexible tightening member due to the rotation of the stent-graft, thereby preventing failure in releasing the stent-graft because of the uncertainty of the state of the flexible tightening member and ensuring that the stent-graft can be released successfully.

(6) In the delivery and release device for stent-graft of the present invention, the outer tube displacement regulating mechanism comprises a front stopper, an outer shell, a rear stopper, and a regulating means provided on the exterior of the outer shell for controlling the displacement of the outer tube, one end of the outer shell is fixedly connected to the front stopper coaxially, and the other end of the outer shell is fixedly connected to the rear stopper coaxially, the supporting tube holder is disposed inside the outer shell and in fixed connection with the outer shell, the regulating means is disposed between the front stopper and the rear stopper, the rear ends of the outer tube and the positioning tube are respectively connected to the regulating means, and the regulating means is operable to be adjusted to move along the outer shell, so as to drive the outer tube to move axially. When the regulating means is adjusted to move along the outer shell, the front stopper and the rear stopper is used to control the moving range of the regulating means not to surpass the outer shell, so as to control the regulating means more conveniently, and the supporting tube holder is in fixed connection with the outer shell, so as to confine the position of the supporting tube and the positioner connected thereto, thereby preventing the stent-graft from moving backwards in the axial direction.

(7) In the delivery and release device for stent-graft of the present invention, the regulating means comprises an outer motion-transmission sleeve and an inner motion-transmission sleeve sleeving on the outer shell, and an outer tube holder fixedly connected to a rear end of the outer tube, the inner motion-transmission sleeve is disposed inside the outer motion-transmission sleeve and the two motion-transmission sleeves are engaged in a threaded connection, the outer tube holder is sheathed inside the outer shell and provided with connectors fixedly connected on both sides thereof, the outer shell is provided with elongated apertures formed thereon and extending in the axial direction, and the connectors extend through the elongated apertures to be connected to the inner motion-transmission sleeve. While being utilized, axial sliding of the outer motion-transmission sleeve is performed in cooperation with twisting of the outer motion-transmission sleeve relative to the inner motion-transmission sleeve in order to drive the outer tube to move axially, and when the latter way is performed, initially the front stopper is used to push against the front end of the outer motion-transmission sleeve, then the outer motion-transmission sleeve is twisted in the forward direction relative to the inner motion-transmission sleeve to drive the inner motion-transmission sleeve to move backwards in the axial direction, so as to withdraw the outer tube backwards to release the distal end of the stent-graft, after the distal end of the stent-graft is released, the outer motion-transmission sleeve is pulled backwards until its rear end is placed against the rear stopper, then the outer motion-transmission sleeve is twisted in the backward direction relative to the inner motion-transmission sleeve to drive the inner motion-transmission sleeve to move forwards in the axial direction until the initial relative position of the inner and outer motion-transmission sleeves is restored. The way of releasing the distal end of the stent-graft by torque transmission is able to precisely control the axial movement of the outer tube, so as to precisely control the release process of the distal end of the stent-graft.

(8) In the delivery and release device for stent-graft of the present invention, the central tube displacement regulating mechanism is provided at the rear side of the outer tube displacement regulating mechanism and comprises a central tube positioning sleeve and a regulating rotary handle, the rear end of the central tube is fixed inside the central tube positioning sleeve, the regulating rotary handle is arranged to sleeve on the exterior of the central tube positioning sleeve and is in a threaded connection therewith; one end of the central tube positioning sleeve is fixedly connected to a rear end of the outer shell and provided with elongated apertures formed thereon and extending in the axial direction of the central tube, connectors are formed on an outer periphery of the central tube at its rear end, the connectors extend through the elongated apertures on the central tube positioning sleeve to be sheathed inside the regulating rotary handle, and the regulating rotary handle is operable to be rotated, so as to drive the central tube to move axially. While being utilized, the regulating rotary handle is rotated relative to the central tube positioning sleeve to drive the central tube to move axially, so as to control the central tube to move axially more precisely, thereby controlling the release process of the stent-graft more precisely.

(9) In the delivery and release device for stent-graft of the present invention, the tightening and releasing means further comprises a releasing member connected to the larger end of the guiding head, one end of the flexible tightening member is connected to the front fixator, while the other end of the flexible tightening member passes through the proximal end of the stent-graft and is detachably connected to the releasing member; while being utilized, the releasing member is detached from the flexible tightening member, driven by the axial movement of the guiding head, thereby releasing the stent-graft. When loading the stent-graft into the delivery and release device, one end of the flexible tightening member is connected to the front fixator, the other end of the flexible tightening member passes through the projecting loop at the proximal end of the stent-graft, tightens the stent-graft and then is detachably connected to one end of the releasing member, while the other end of the releasing member is connected to the guiding head; when releasing the stent-graft, the central tube drives the guiding head and the releasing member to move axially, and the flexible tightening member is relatively stationary as it is fixedly connected to the front fixator, after the movement reaches a certain extent, the releasing member is detached from the flexible tightening member, meanwhile the stent-graft becomes free from the constraining of the flexible tightening member and unfolds under its own elastic force to complete the release process.

(10) In the delivery and release device for stent-graft of the present invention, a through hole is axially formed through the front fixator, and adapted for detachably connecting the front fixator to the bar-shaped body. When loading the stent-graft, the bar-shaped body is detachably connected into the through hole in order to prevent the guiding head from rotating and to make the structure of the front end of the delivery and release device more compact, which helps to ensure that the state of relative connection of the string-shaped body and the bar-shaped body does not change due to the rotation of the guiding head when assembling the device, avoids the phenomenon of crossing or knotting of the string-shaped body because of the guiding head driving the bar-shaped body to rotate, and ensures successful releasing of the stent-graft.

(11) In the delivery and release device for stent-graft of the present invention, the bar-shaped body is a metal bar connected to the end face of the larger end of the guiding head and positioned circumferentially on the end face, and the string-shaped body is a ring suture, the ring suture is detachably connected to the metal bar by sleeving. When loading the stent-graft, one end of the ring suture is connected to the front fixator, the other end of the ring suture passes through the projecting loop at the proximal end of the stent-graft, tightens the stent-graft and then sleeves onto one end of the metal bar, while the other end of the metal bar is fixedly connected to the guiding head; when releasing the stent-graft, the central tube drives the metal bar to move axially, and the ring suture is relatively stationary as it is fixedly connected to the front fixator, after the movement reaches a certain extent, the metal bar is detached from the ring suture, meanwhile the stent-graft becomes free from the constraining of the ring suture and unfolds under the action of its own elastic force to complete the release process.

(12) In the delivery and release device for stent-graft of the present invention, a reinforcement tube is arranged to sleeve on an outer periphery of the supporting tube, one end of the reinforcement tube extends through the outer tube holder and is placed inside the front stopper, while the other end of the reinforcement tube is fixedly connected to a reinforcement tube holder, and the reinforcement tube holder is fixed inside the outer shell and close to the supporting tube holder. The reinforcement tube is used to support and reinforce the supporting tube, so as to prevent deformation or fracture of the supporting tube during operation because of its large length-diameter ratio which might affect the utilization of the delivery and release device; the reinforcement tube is fixedly connected to the outer shell by the reinforcement tube holder.

(13) In the delivery and release device for stent-graft of the present invention, the central tube positioning sleeve is integrally formed with the outer shell, each end of the central tube positioning sleeve is provided with a hoop connected and sleeving thereon, with one hoop arranged to sleeve on the rear end of the outer shell and with the other hoop arranged to sleeve on the tail end of the central tube positioning sleeve. The arrangement of the hoops makes it convenient to disassemble, repair and assemble the delivery and release device.

BRIEF DESCRIPTION OF THE DRAWINGS

Detailed description of specific embodiments of the present invention is presented below, with reference of accompanying drawings.

FIG. 12A is a sectional view according to one embodiment of the present invention;

FIG. 12B is a sectional view according to one embodiment of the present invention;

FIG. 13 is a sectional view in a plane perpendicular to that of FIGS. 12A-12B according to one embodiment of the present invention;

Figure 1:
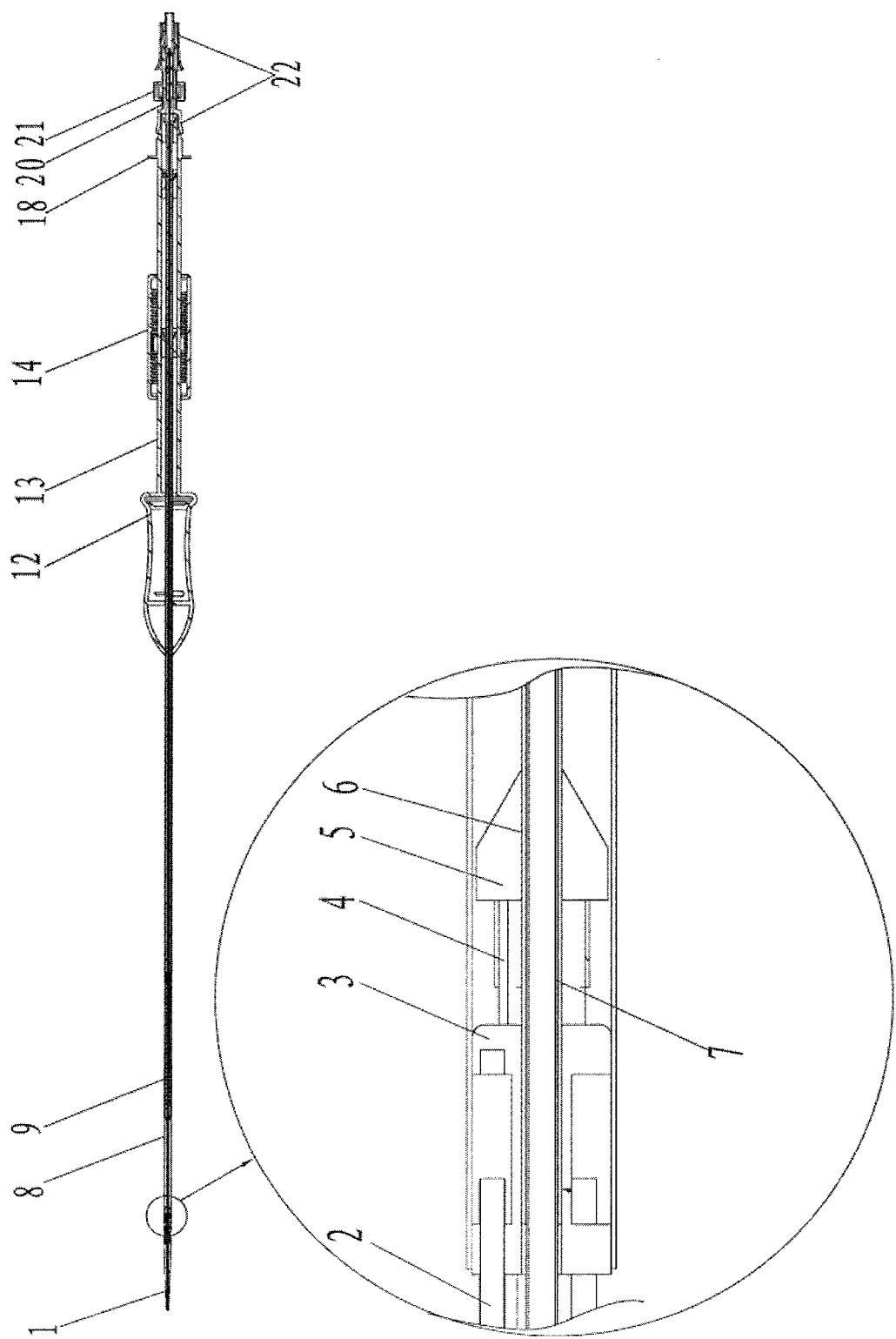
FIG. 1 shows a delivery and release device for stent-graft of the present invention, with a drawing of partial enlargement.
Figure 2:
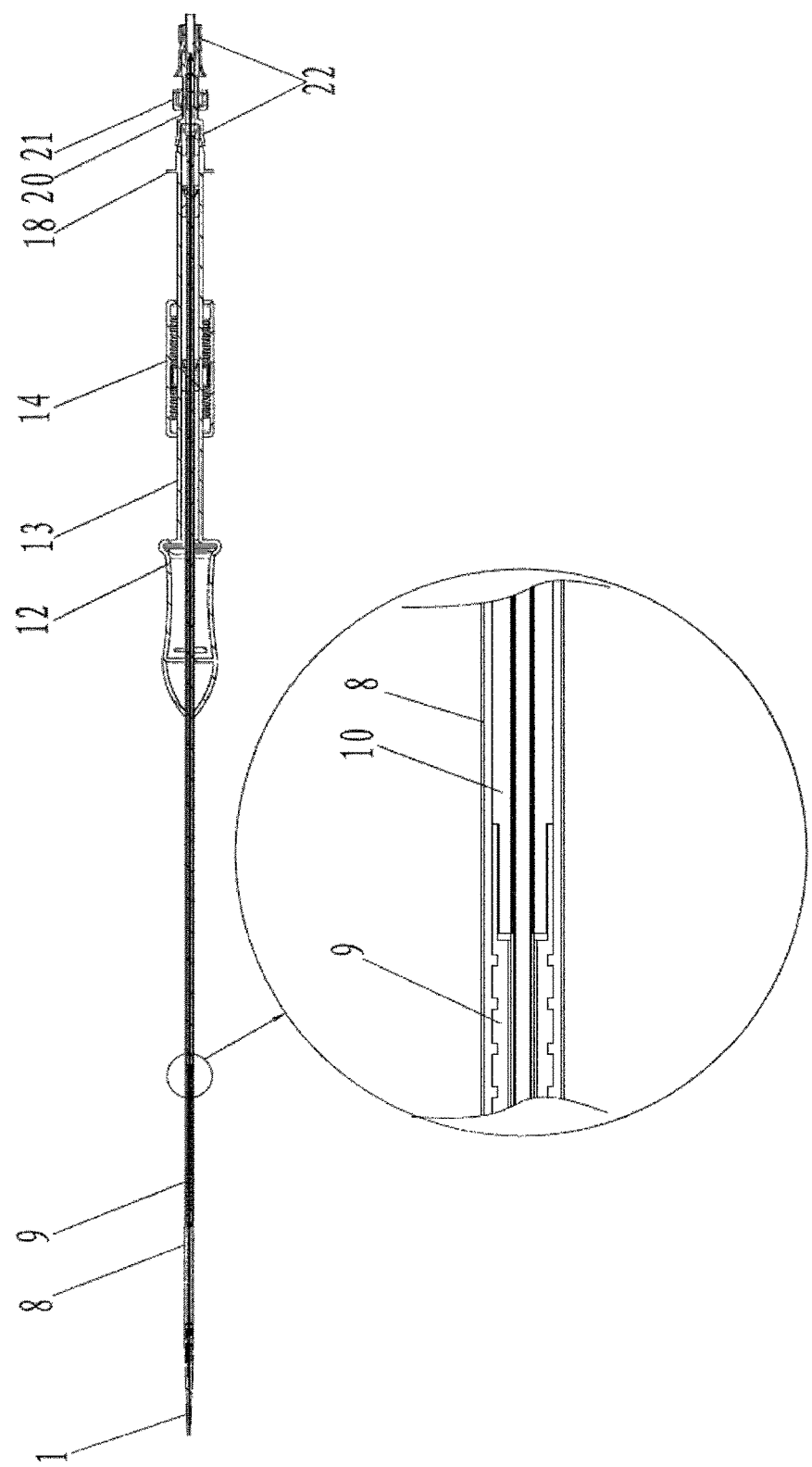
FIG. 2 shows a delivery and release device for stent-graft of the present invention, with a drawing of partial enlargement.
Figure 3:
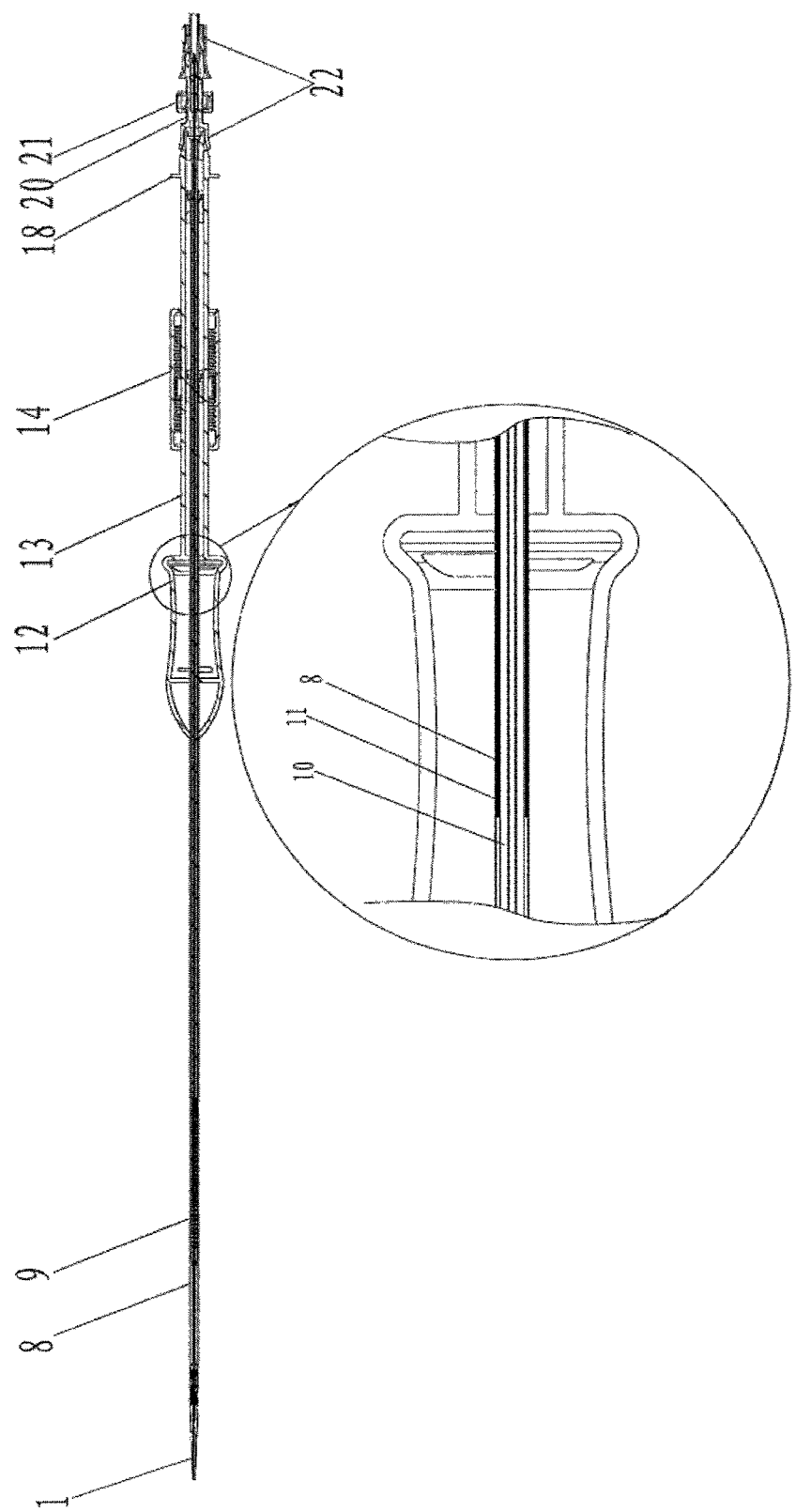
FIG. 3 shows a delivery and release device for stent-graft of the present invention, with a drawing of partial enlargement.
Figure 4:
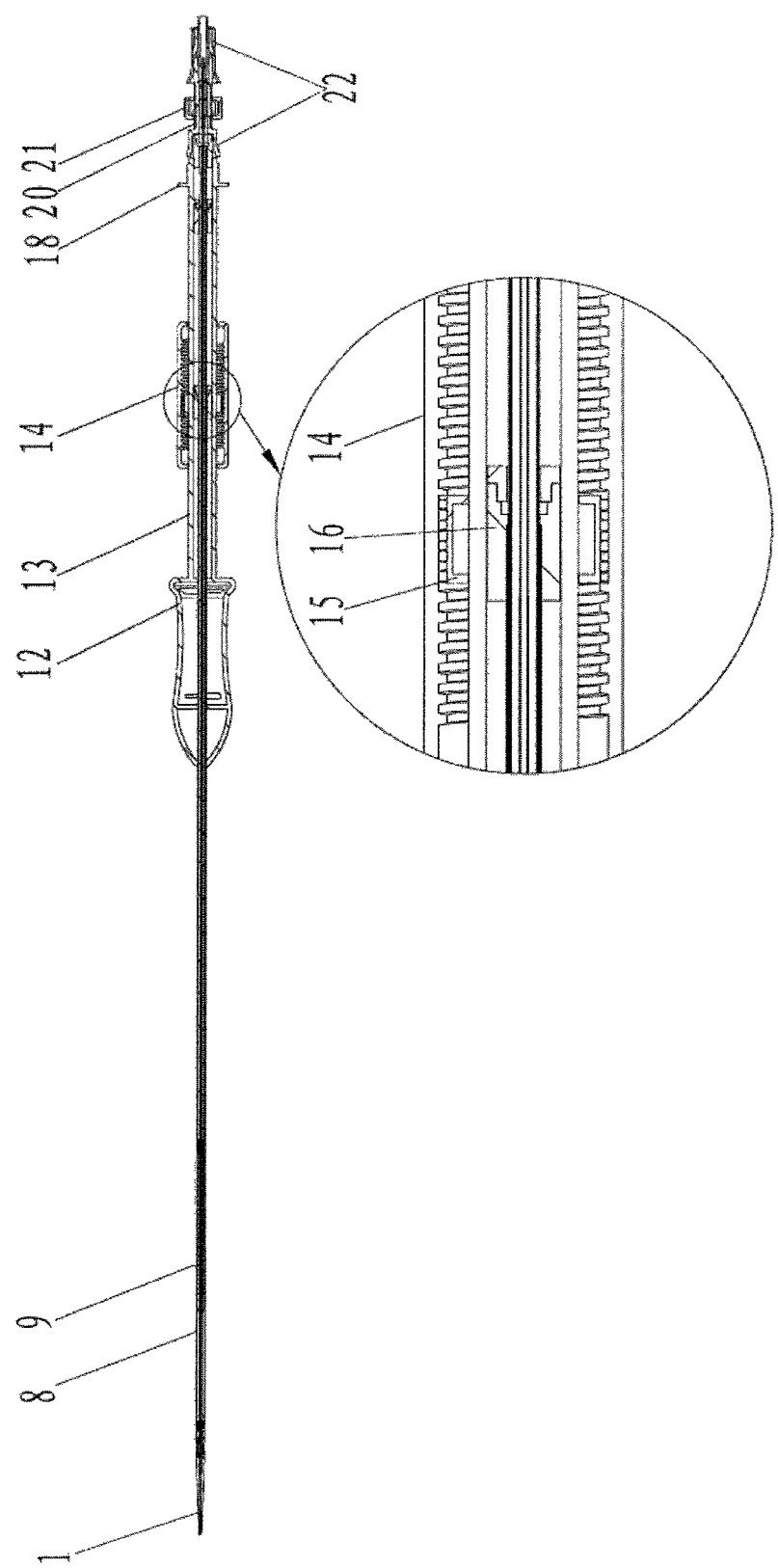
FIG. 4 shows a delivery and release device for stent-graft of the present invention, with a drawing of partial enlargement.
Figure 5:
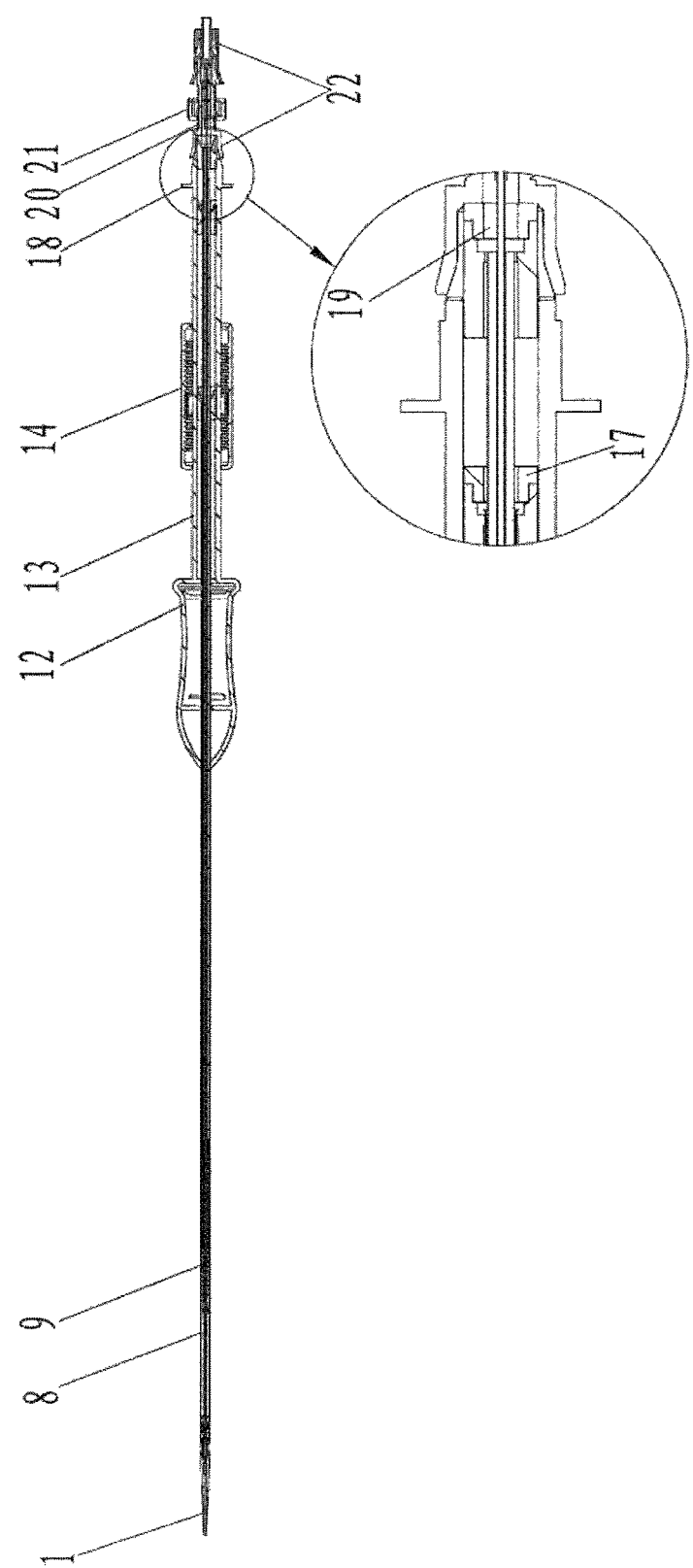
FIG. 5 shows a delivery and release device for stent-graft of the present invention, with a drawing of partial enlargement.

The markings in the drawings are explained as follows:

1—guiding head, 2—metal bar, 3—front fixator, 4—rear fixator, 5—conical anti-rotation member, 6—positioning tube, 7—central tube, 8—outer tube, 9—positioner, 10—supporting tube, 11—reinforcement tube, 12—front stopper, 13—outer shell, 14—outer motion-transmission sleeve, 15—inner motion-transmission sleeve, 16—outer tube holder, 17—reinforcement tube holder, 18—rear stopper, 19—supporting tube holder, 20—central tube positioning sleeve, 21—regulating rotary handle, 22—hoop.

DETAILED DESCRIPTION OF EMBODIMENTS

The delivery and release device for stent-graft of the present invention comprises: a cone-shaped guiding head 1, with a hollow passage formed axially therein; a central tube 7, one end of which is fixedly connected to a larger end of the guiding head 1 and communicated with the hollow passage of the guiding head 1; an outer tube 8, sleeving on the exterior of the central tube 7, and operable to slide along the exterior of the central tube 7; a fixator, sheathed between the central tube 7 and the outer tube 8, with an outer periphery of the central tube 7 close to the larger end of the guiding head 1 sheathed by the fixator, and with an outer periphery of the fixator coordinating with an inner periphery of the outer tube 8 in a sliding manner; a positioning mechanism for positioning the stent-graft; an outer tube displacement regulating mechanism, sleeving on an outer periphery of the outer tube 8 at an operation side, and adapted for controlling the axial movement of the outer tube 8; a central tube displacement regulating mechanism, sleeving on the central tube 7 at an operation side, and adapted for controlling the axial movement of the central tube 7; wherein, a tightening and releasing means for the stent-graft is provided at the larger end of the guiding head 1, the tightening and releasing means comprises a flexible tightening member, the flexible tightening member is connected to the larger end of the guiding head 1 for tightening the stent-graft, and the central tube 7 is operable to control the guiding head 1 to move in the axial direction of the central tube 7, so as to detach the flexible tightening member from the stent-graft, thereby releasing the stent-graft.

Further, the positioning mechanism comprises a positioning tube 6 and a positioned 9, the positioning tube 6 is sheathed between the fixator and the central tube 7 and extends through the fixator, the positioned 9 is sheathed between the positioning tube 6 and the outer tube 8, with an outer periphery of the positioning tube 6 at a rear side of the stent-graft sheathed by the positioner 9, and with an outer periphery of the positioner 9 coordinating with an inner periphery of the outer tube 8 in a sliding manner.

In order to constrain the position of the positioner 9 and thus constrain the position of the rear end of the stent-graft, the delivery and release device preferably further comprises a supporting mechanism, which comprises a supporting tube 10 sheathed between the positioning tube 6 and the outer tube 8, and a supporting tube holder 19, with one end of the supporting tube 10 fixedly connected to the rear end of the positioner 9 and the other end connected to the outer tube displacement regulating mechanism by the supporting tube holder 19. Further, the positioner 9 is a hollow tubular structure, with texture formed on its outer periphery, the central tube 7 and the positioning tube 6 extend through the positioner 9.

In order to prevent the stent-graft from rotating and thus keep the flexible tightening member at the state of tightening the stent-graft, the fixator preferably comprises a front fixator 3 and a rear fixator 4, the front fixator 3 and the rear fixator 4 are sheathed between the positioning tube 6 and the outer tube 8 respectively at the front side and at the rear side, the rear fixator 4 is provided with a conical anti-rotation member 5 at its rear end for preventing the stent-graft from rotating, the conical anti-rotation member 5 is sheathed between the positioning tube 6 and the outer tube 8, and a plurality of anti-rotation recesses are formed axially on an outer periphery of the conical anti-rotation member 5.

Further, the outer tube displacement regulating mechanism preferably comprises a front stopper 12, an outer shell 13, a rear stopper 18, and a regulating means provided on the exterior of the outer shell 13 for controlling the displacement of the outer tube 8, one end of the outer shell 13 is fixedly connected to the front stopper 12 coaxially, and the other end of the outer shell 13 is fixedly connected to the rear stopper 18 coaxially, the supporting tube holder 19 is disposed inside the outer shell 13 and in fixed connection with the outer shell 13; the regulating means is disposed between the front stopper 12 and the rear stopper 18, the rear ends of the outer tube 8 and the positioning tube 6 are respectively connected to the regulating means, and the regulating means is operable to be adjusted to move along the outer shell 13, so as to drive the outer tube 8 to move axially.

Further, in order to control the outer tube 8 to move in the axial direction more precisely, the regulating means preferably comprises an outer motion-transmission sleeve 14 and an inner motion-transmission sleeve 15 sleeving on the outer shell 13, and an outer tube holder 16 fixedly connected to a rear end of the outer tube 8, the inner motion-transmission sleeve 15 is disposed inside the outer motion-transmission sleeve 14 and the two motion-transmission sleeves are engaged in a threaded connection, the outer tube holder 16 is sheathed inside the outer shell 13 and provided with connectors fixedly connected on both sides thereof, the outer shell 13 is provided with elongated apertures formed thereon and extending in the axial direction, and the connectors extend through the elongated apertures to be connected to the inner motion-transmission sleeve 15.

In order to precisely control the central tube 7 to move axially and thus accurately control the release process of the stent-graft, preferably, the central tube displacement regulating mechanism is provided at the rear side of the outer tube displacement regulating mechanism and comprises a central tube positioning sleeve 20 and a regulating rotary handle 21, the rear end of the central tube 7 is fixed inside the central tube positioning sleeve 20, the regulating rotary handle 21 is arranged to sleeve on the exterior of the central tube positioning sleeve 20 and is in a threaded connection therewith; one end of the central tube positioning sleeve 20 is fixedly connected to a rear end of the outer shell 13 and provided with elongated apertures formed thereon and extending in the axial direction of the central tube 7, connectors are formed on an outer periphery of the central tube 7 at its rear end, the connectors extend through the elongated apertures on the central tube positioning sleeve 20 to be sheathed inside the regulating rotary handle 21, and the regulating rotary handle 21 is operable to be rotated, so as to drive the central tube 7 to move axially.

Figures 14A, 14B:
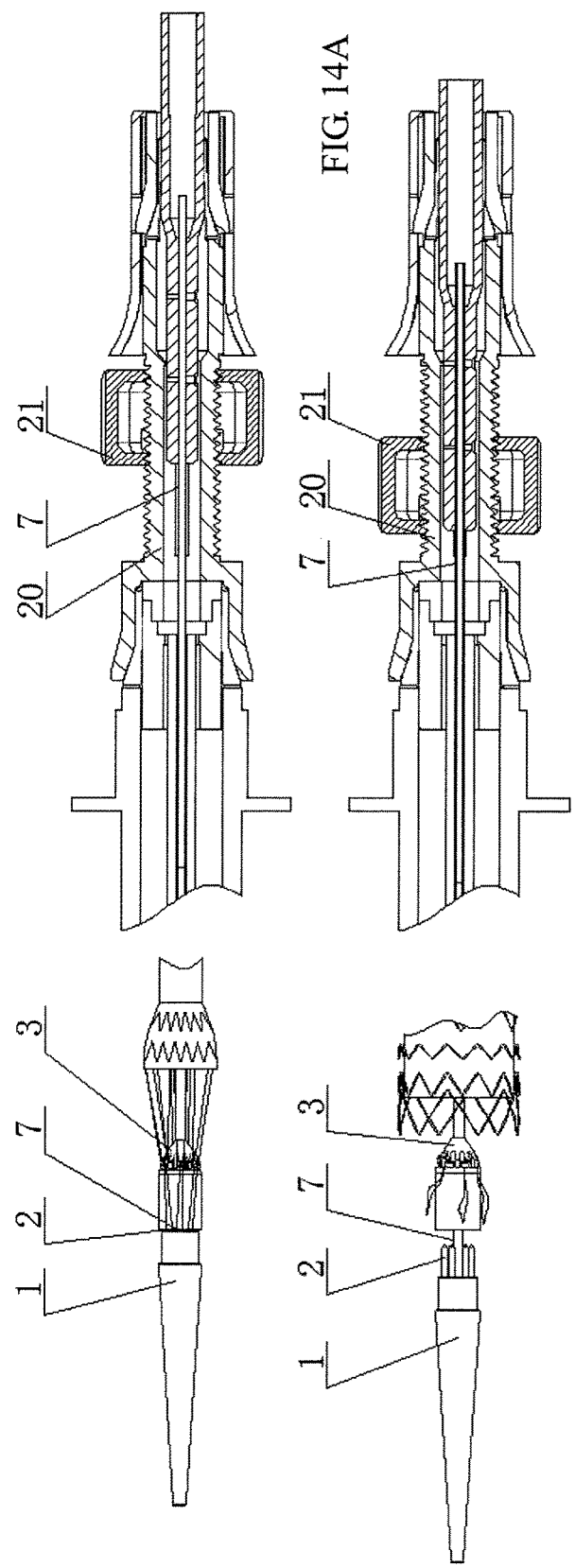
FIG. 14A is a sectional view according to one embodiment of the present invention.
FIG. 14B is a sectional view according to one embodiment of the present invention.
Figure 15:
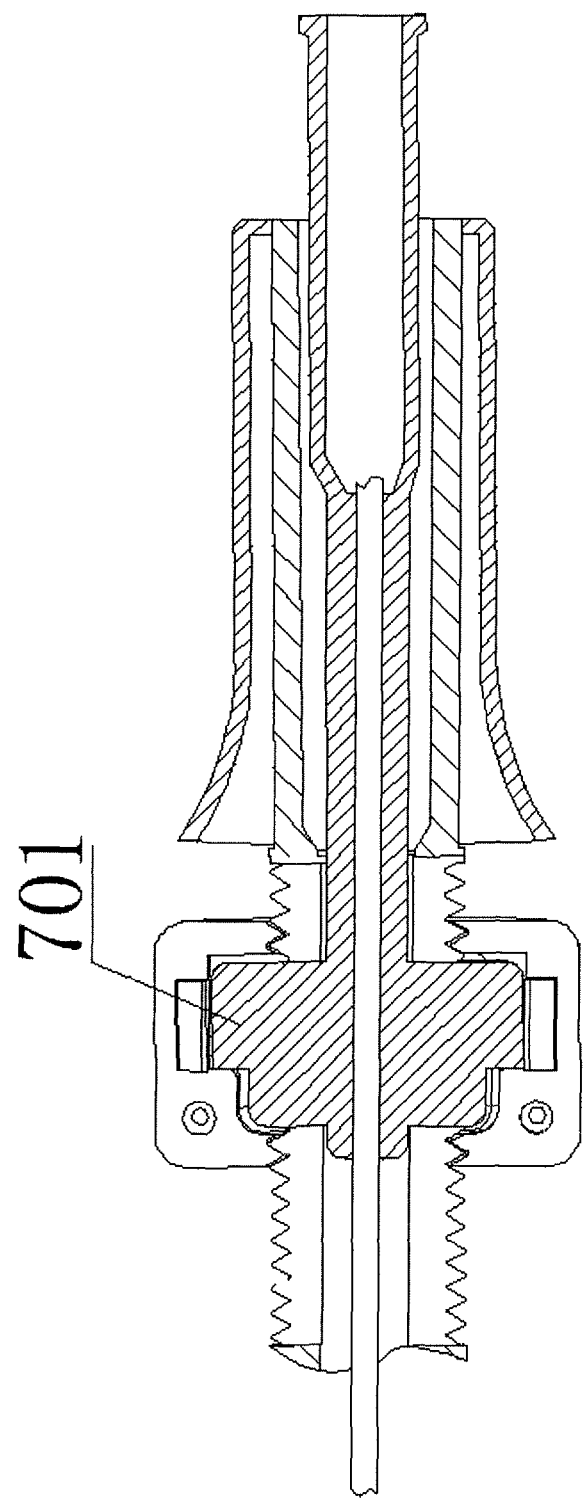
FIG. 15 is a sectional view in a plane perpendicular to that of FIGS. 14A-14B according to one embodiment of the present invention.

FIG. 12A shows the outer tube displacement regulating mechanism in a status before the outer tube 8 is proximally withdrawn, FIG. 12B shows the outer tube displacement regulating mechanism in a status after the outer tube 8 is proximally withdrawn, FIG. 13 shows the connectors 1601 on the outer tube holder 16, FIG. 14A shows the central tube displacement regulating mechanism in a status before the central tube 7 is distally moved, FIG. 14B shows the central tube displacement regulating mechanism in a status after the central tube 7 is distally moved, and FIG. 15 shows the connectors 701 on the outer periphery of the central tube 7.

As an alternative way of implementation, in order to make the release process of the stent-graft more convenient to operate, the tightening and releasing means preferably further comprises a releasing member connected to the larger end of the guiding head 1, one end of the flexible tightening member is connected to the front fixator 3, while the other end of the flexible tightening member passes through a proximal end of the stent-graft and is detachably connected to the releasing member; while being utilized, the releasing member is detachable from the flexible tightening member, driven by the axial movement of the guiding head 1, so as to release the stent-graft.

Alternatively, the tightening and releasing means may preferably further comprise a releasing member connected to the front fixator 3, one end of the flexible tightening member is connected to the larger end of the guiding head 1, while the other end of the flexible tightening member passes through a proximal end of the stent-graft and is detachably connected to the releasing member by tying, sleeving, buckling or magnetic attraction; while being utilized, the flexible tightening member is detachable from the releasing member, driven by the axial movement of the guiding head 1, so as to release the stent-graft.

Further, the flexible tightening member is preferably detachably connected to the releasing member by tying, sleeving, buckling or magnetic attraction.

Figure 6:
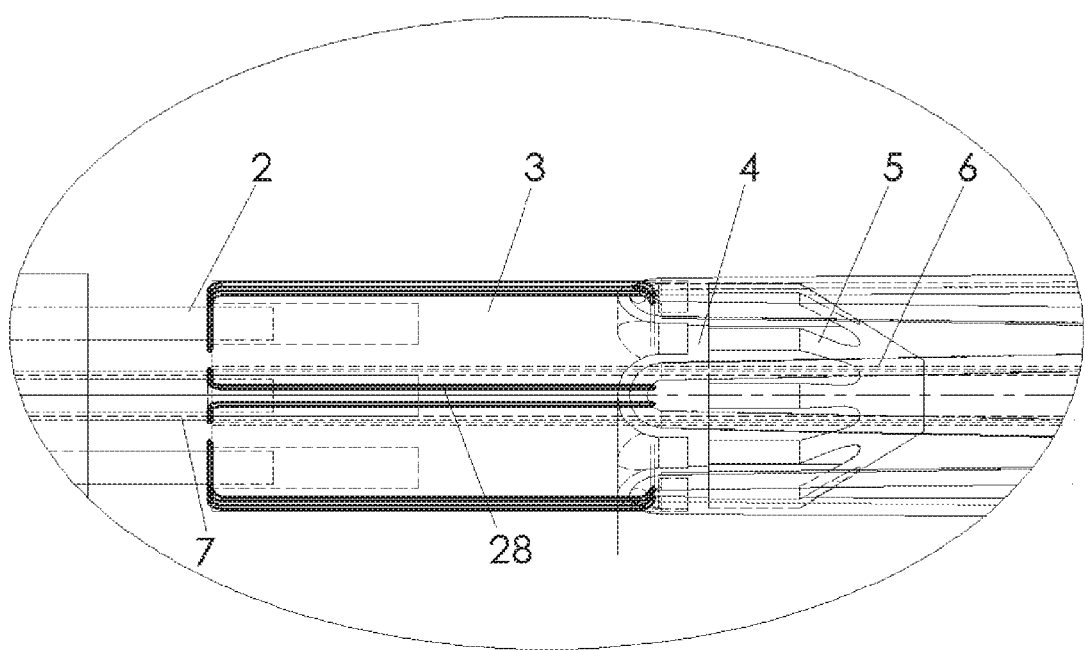
FIG. 6 is a partial enlargement of a delivery and release device for stent-graft of the present invention.

Further, the releasing member is preferably a bar-shaped body extending in the axial direction of the central tube 7, and one end of the bar-shaped body is connected to the end face of the larger end of the guiding head 1, while the other end of the bar-shaped body is detachably connected to the flexible tightening member; the flexible tightening member is a string-shaped body 28, as illustrated in FIG. 6, and one end of the string-shaped body 28 is connected to the front fixator 3, while the other end of the string-shaped body 28 passes through a proximal end of the stent-graft and is detachably connected to the bar-shaped body; while being utilized, the bar-shaped body is detachable from the string-shaped body 28, driven by the axial movement of the guiding head 1, so as to release the stent-graft.

As an alternative way of implementation, in order to prevent the guiding head 1 from rotating so as to keep the bar-shaped body and the string-shaped body in connected state and prevent the string-shaped body from crossing or knotting, A through hole is preferably axially formed through the front fixator 3, and adapted for detachably connecting the front fixator 3 to the bar-shaped body.

Figure 7:
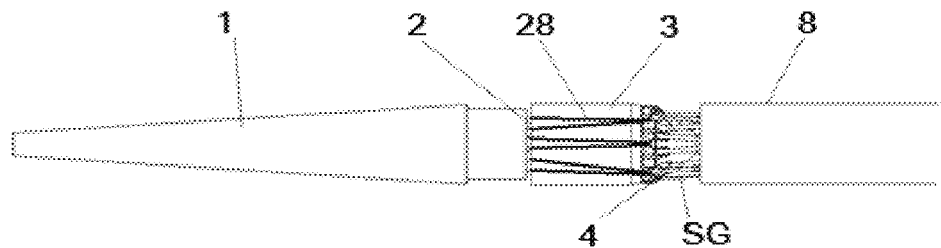
FIG. 7 is a plan view according to one embodiment of the present invention.
Figure 8:
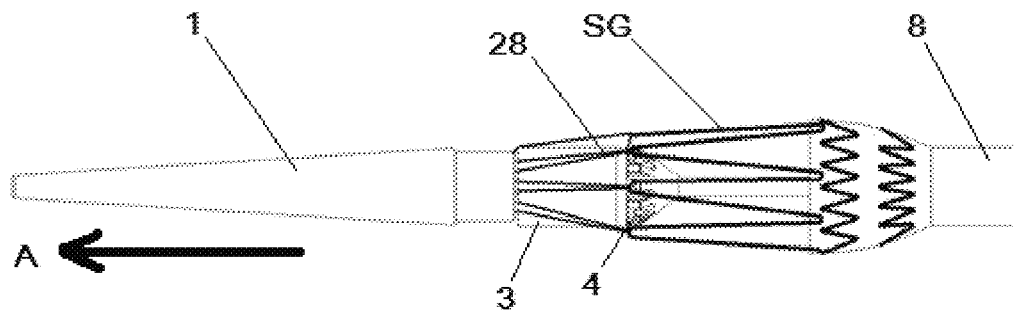
FIG. 8 is a plan view according to one embodiment of the present invention.
Figure 9:
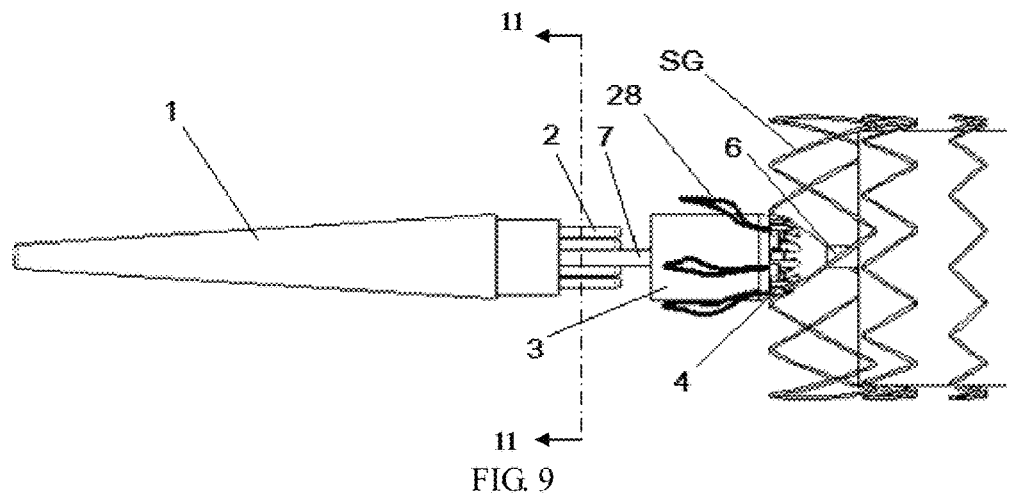
FIG. 9 is a plan view according to one embodiment of the present invention.
Figure 10:
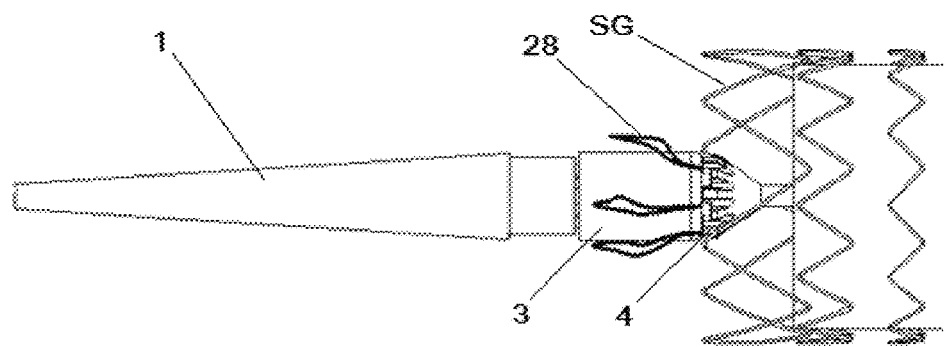
FIG. 10 is a plan view according to one embodiment of the present invention.
Figure 11:
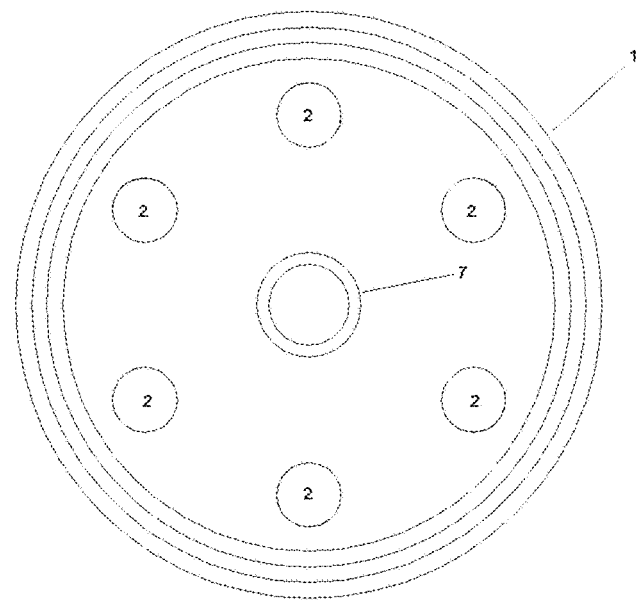
FIG. 11 is a sectional view taken at line 11-11 in FIG. 9 according to one embodiment of the present invention.

Further, as shown in FIGS. 7-11, the bar-shaped body preferably includes a plurality of metal bars 2 fixedly connected and distributed in a circumferential manner on the end face of the larger end of the guiding head 1, and the string-shaped body includes a plurality of ring sutures 28, and each of the ring sutures 28 passes through a bare stent SG at the proximal end of the stent-graft and has one loop end fixedly connected on the front fixator 3 and the other loop end detachably connected to a corresponding one of said metal bars 2. In a tightened state as shown in FIG. 7, the plurality of metal bars 2 engage the plurality of ring sutures 28 to tighten the bare stent SG at the proximal end of the stent-graft in a radially inward direction. The central tube is operable to control the guiding head 1 and the plurality of metal bars 2 fixedly connected thereon to move forward in the axial direction of the central tube as shown by the arrow "A" in FIG. 8, so as to drive the plurality of metal bars 2 to detach from the plurality of ring sutures 28, thereby releasing the bare stent SG at proximal end of the stent-graft.

Further, a reinforcement tube 11 is preferably arranged to sleeve on an outer periphery of the supporting tube 10, one end of the reinforcement tube 11 extends through the outer tube holder 16 and is placed inside the front stopper 12, while the other end of the reinforcement tube 11 is fixedly connected to a reinforcement tube holder 17, and the reinforcement tube holder 17 is fixed inside the outer shell 13 and close to the supporting tube holder 19.

As shown in FIGS. 1-5, the central tube positioning sleeve 20 is preferably integrally formed with the outer shell 13, each end of the central tube positioning sleeve 20 is provided with a hoop 22 connected and sleeving thereon, with one hoop 22 arranged to sleeve on the rear end of the outer shell 13 and with the other hoop 22 arranged to sleeve on the tail end of the central tube positioning sleeve 20.

In the treatment of aortic aneurysm or aortic dissection, the operation process of the delivery and release device for stent-graft of the present invention is as follows:

Prior to the surgical operation, the front stopper 12 of the delivery and release device for stent-graft is pushed against the front end of the outer motion-transmission sleeve 14, meanwhile the outer motion-transmission sleeve 14 is twisted in the forward direction to allow the inner motion-transmission sleeve 15 to drive the outer tube 8 to move backwards so as to expose the space for placing the stent-graft, then, the stent-graft is sheathed onto the positioning tube 6, the ring suture connected to the front fixator 3 is guided through the projecting loop at the proximal end of the stent-graft and tightened onto the metal bar 2 by sleeving, meanwhile the tightened stent-graft is fixed in position by the fixator and the positioner 9, then, the outer motion-transmission sleeve 14 is pulled backwards until the rear end of the outer motion-transmission sleeve 14 is placed against the rear stopper 18, and the outer motion-transmission sleeve 14 is twisted in the backward direction to allow the inner motion-transmission sleeve 15 to move forwards to come to the initial relative position of the inner and outer motion-transmission sleeves, then, the outer motion-transmission sleeve 14 is pushed forwards, so as to allow the outer tube 8 to come to its initial position where the outer tube 8 completely covers the fixator, the stent-graft and the positioner 9.

During the surgical operation, firstly, the right femoral artery is punctured and a guiding wire is inserted, then, the delivery and release device for stent-graft is guided into the aorta along the guiding wire. Under surveillance of X-ray monitoring equipment, the delivery and release device for stent-graft is moved nearby the diseased region, then, the front stopper 12 is pushed against the front end of the outer motion-transmission sleeve 14 and the outer motion-transmission sleeve 14 is twisted in the forward direction slowly, so that the outer tube 8 is driven by the outer motion-transmission sleeve 14 through the inner motion-transmission sleeve 15 to move axially backwards until the outer tube 8 is completely detached from the stent-graft, at this state, the distal end of the stent-graft unfolds without constraining of the outer tube 8, but the proximal end of the stent-graft is still constrained at the location of the metal bar and the front fixator 3; the delivery and release device is moved to the most suitable position for release, then, the regulating rotary handle 21 is rotated to allow the central tube 7 to drive the guiding head 1 and the metal bar 2 to move forwards, and after moving for a certain distance, the metal bar 2 is detached from the ring suture, causing the proximal end of the stent-graft to be detached from the ring suture and to unfold automatically under its own tension force, thus the stent-graft is completely detached from the delivery and release device and the release process is completed, finally, the delivery and release device for stent-graft is withdrawn from the human body along the guiding wire.

The present invention has been illustrated in details through the aforementioned specific embodiments, however, those skilled in the art should understand that, any modifications in forms or particulars based on these embodiments within the claimed scope of the appended claims are all intended to be embraced within the protection scope of the present invention.

The invention claimed is:

1. A delivery and release device for stent-graft, comprising:

a guiding head, in the shape of a cone, and provided with a hollow passage formed axially therein;

a central tube, one end of which is fixedly connected to a larger end of the guiding head and communicated with the hollow passage of the guiding head;

an outer tube, sleeving on the exterior of the central tube, and operable to slide along the exterior of the central tube;

a fixator, sheathed between the central tube and the outer tube, with an outer periphery of the central tube close to the larger end of the guiding head sheathed by the fixator, and with an outer periphery of the fixator coordinating with an inner periphery of the outer tube in a sliding manner;

a positioning mechanism, adapted for positioning the stent-graft, the positioning mechanism comprises a positioning tube and a positioner, the positioning tube is sheathed between the fixator and the central tube and extends through the fixator, the positioner is sheathed between the positioning tube and the outer tube, with an outer periphery of the positioning tube at a rear side of the stent-graft sheathed by the positioner, and with an outer periphery of the positioner coordinating with an inner periphery of the outer tube in a sliding manner;

an outer tube displacement regulating mechanism, sleeving on an outer periphery of the outer tube at an operation side, and adapted for controlling the axial movement of the outer tube;

a central tube displacement regulating mechanism, sleeving on the central tube at an operation side, and adapted for controlling the axial movement of the central tube;

wherein, the fixator comprises a front fixator and a back fixator, the front fixator and the back fixator are sheathed between the positioning tube and the outer tube respectively at the front side and at the rear side, the back fixator is provided with a conical anti-rotation member at its rear end for preventing the stent-graft from rotating, the conical anti-rotation member is sheathed between the positioning tube and the outer tube, and a plurality of anti-rotation recesses are formed axially on an outer periphery of the conical anti-rotation member, a tightening and releasing means for the stent-graft, comprises a flexible tightening member and a releasing member, the releasing member includes a plurality of metal bars fixedly connected and distributed in a circumferential manner on the end face of the larger end of the guiding head, and each of the metal bars extends in a direction parallel to the axial direction of the central tube, the flexible tightening member includes a plurality of ring sutures, and each of the ring sutures passes through a bare stent at the proximal end of the stent-graft and has one loop end fixedly connected on the front fixator and the other loop end detachably connected to a corresponding one of said metal bars, in a tightened state, the plurality of metal bars engage the plurality of ring sutures to tighten the bare stent at the proximal end of the stent-graft in a radially inward direction, and the central tube is operable to control the guiding head and the plurality of metal bars fixedly connected thereon to move forward in the axial direction of the central tube, to drive the plurality of metal bars to detach from the plurality of ring sutures and cause the plurality of ring sutures to detach from the bare stent, thereby releasing the bare stent at proximal end of the stent-graft.

2. The delivery and release device for stent-graft of claim 1, wherein,
the positioner is a hollow tubular structure, with texture formed on its outer periphery, the central tube and the positioning tube extend through the positioner.

3. The delivery and release device for stent-graft of claim 1, wherein,
a through hole is axially formed through the front fixator, and adapted for detachably connecting the front fixator to the bar-shaped body.

4. The delivery and release device for stent-graft of claim 1, further comprising a supporting mechanism, the supporting mechanism comprises a supporting tube sheathed between the positioning tube and the outer tube, and a supporting tube holder, with one end of the supporting tube fixedly connected to the rear end of the positioner and the other end connected to the outer tube displacement regulating mechanism by the supporting tube holder.

5. The delivery and release device for stent-graft of claim 4, wherein,
the outer tube displacement regulating mechanism comprises a front stopper, an outer shell, a rear stopper, and a regulating means provided on the exterior of the outer shell for controlling the displacement of the outer tube;
one end of the outer shell is fixedly connected to the front stopper coaxially, and the other end of the outer shell is fixedly connected to the rear stopper coaxially;
the supporting tube holder is disposed inside the outer shell and in fixed connection with the outer shell;
the regulating means is disposed between the front stopper and the rear stopper;
the rear ends of the outer tube and the positioning tube are respectively connected to the regulating means, and the regulating means is operable to be adjusted to move along the outer shell, so as to drive the outer tube to move axially.

6. The delivery and release device for stent-graft of claim 5, wherein,
the regulating means comprises an outer motion-transmission sleeve and an inner motion-transmission sleeve sleeving on the outer shell, and an outer tube holder fixedly connected to a rear end of the outer tube;
the inner motion-transmission sleeve is disposed inside the outer motion-transmission sleeve and the two motion-transmission sleeves are engaged in a threaded connection, the outer tube holder is sheathed inside the outer shell and provided with connectors fixedly connected on both sides thereof;
the outer shell is provided with elongated apertures formed thereon and extending in the axial direction, and the connectors extend through the elongated apertures to be connected to the inner motion-transmission sleeve.

7. The delivery and release device for stent-graft of claim 6, wherein,
a reinforcement tube is arranged to sleeve on an outer periphery of the supporting tube; one end of the reinforcement tube extends through the outer tube holder and is placed inside the front stopper, while the other end of the reinforcement tube is fixedly connected to a reinforcement tube holder; and
the reinforcement tube holder is fixed inside the outer shell and close to the supporting tube holder.

8. The delivery and release device for stent-graft of claim 5, wherein,
the central tube displacement regulating mechanism is provided at the rear side of the outer tube displacement regulating mechanism and comprises a central tube positioning sleeve and a regulating rotary handle;

the rear end of the central tube is fixed inside the central tube positioning sleeve;

the regulating rotary handle is arranged to sleeve on the exterior of the central tube positioning sleeve and is in a threaded connection therewith;

one end of the central tube positioning sleeve is fixedly connected to a rear end of the outer shell and provided with elongated apertures formed thereon and extending in the axial direction of the central tube, connectors are formed on an outer periphery of the central tube at its rear end, the connectors extend through the elongated apertures on the central tube positioning sleeve to be sheathed inside the regulating rotary handle, and the regulating rotary handle is operable to be rotated, so as to drive the central tube to move axially.

9. The delivery and release device for stent-graft of claim 8, wherein, the central tube positioning sleeve is integrally formed with the outer shell, each end of the central tube positioning sleeve is provided with a hoop connected and sleeving thereon, with one hoop arranged to sleeve on the rear end of the outer shell, and with the other hoop arranged to sleeve on the tail end of the central tube positioning sleeve.

* * * * *